United States Patent [19]

McArdle et al.

[11] Patent Number: 4,974,243
[45] Date of Patent: Nov. 27, 1990

[54] POSITIONING SYSTEM FOR A X-RAY TOMOGRAPHY

[75] Inventors: Phillip C. McArdle, San Francisco; Steven P. McEvoy, San Carlos, both of Calif.

[73] Assignee: Axialtome Corporation, San Carlos, Calif.

[21] Appl. No.: 445,760

[22] Filed: Dec. 4, 1989

[51] Int. Cl.⁵ ............................................. A61B 6/14
[52] U.S. Cl. ...................................... 378/38; 378/39; 378/180; 378/205
[58] Field of Search ................... 378/38, 39, 40, 177, 378/178, 180, 205, 208

[56] References Cited

U.S. PATENT DOCUMENTS 4,907,251  3/1990  Mork et al. ........................... 378/38

Primary Examiner—Craig E. Church
Attorney, Agent, or Firm—Donald C. Feix; Thomas M. Freiburger

[57] ABSTRACT

An instrument and system precisely positions a selected cranial implant site for X-ray tomography. The system and method involve first positioning the patient accurately in a straight-ahead reference position using a cephalostat, with the ears positioned in the vertical plane containing all X-ray axes and at a particular reference level which may be the level of horizontal X-ray projection. The apparatus includes a pointer system which pivots on the cephalostat vertical center of rotation to measure the angle to a site of interest on the mandible or maxilla, with an adjustable pointer for measuring the height and radial distance of the site from reference positions. The pointer may be extended to directly contact the site of interest on the patient. The information thus obtained gives polar coordinates of the site. Calculations are made to convert this information to a set of cartesian coordinates for use in repositioning the patient to position the site accurately in the vertical plane and at the tomographic intersection point. An additional calculation is made from a derived formula to determine the angle of tangency to the mandibular arc and the required further adjustment to compensate for this angle. The apparatus includes translating stages for X, Y and Z translational adjustments of the cephalostat to accurately position the patient with the mandible or maxilla site at isocenter with the tangent of the mandibular curve parallel to the central X-ray beam axis.

15 Claims, 20 Drawing Sheets

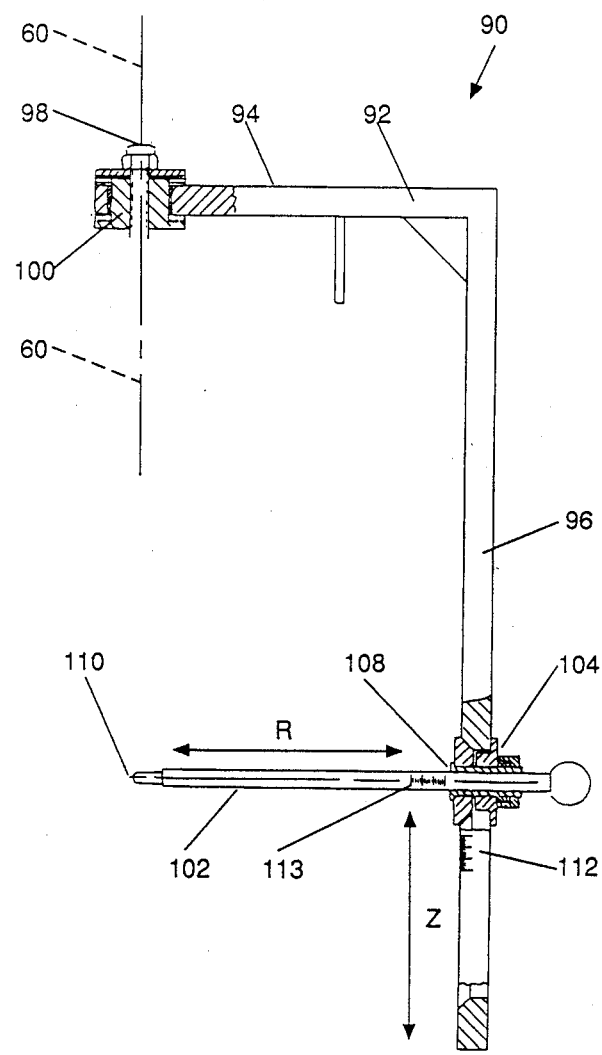
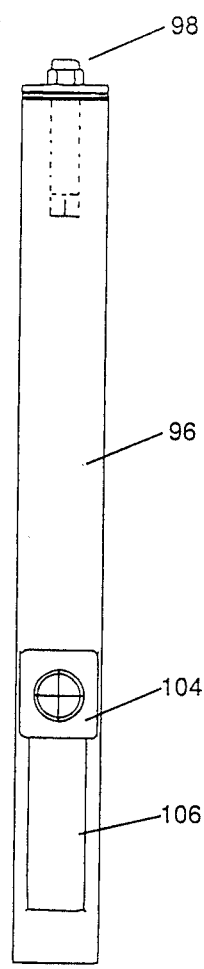
FIG. 6A
FIG. 6B

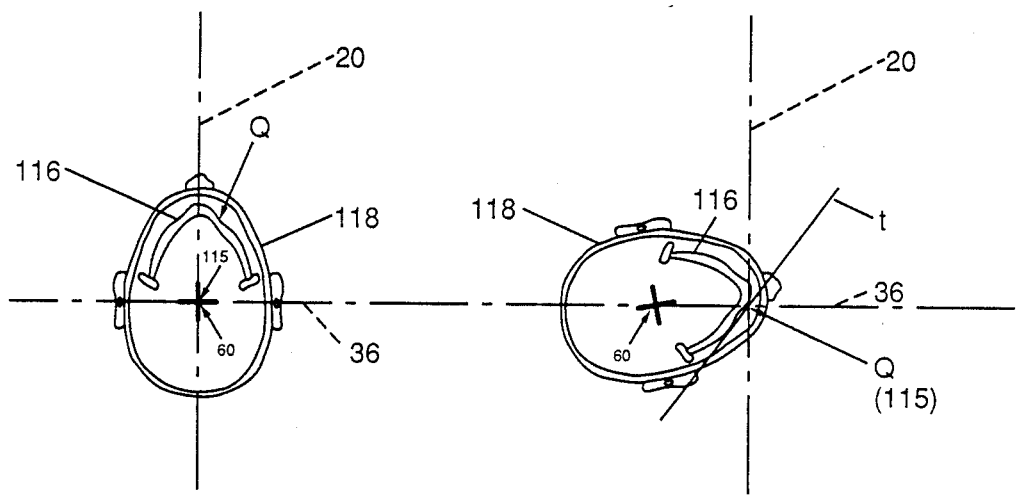
FIG. 7A   FIG. 7B
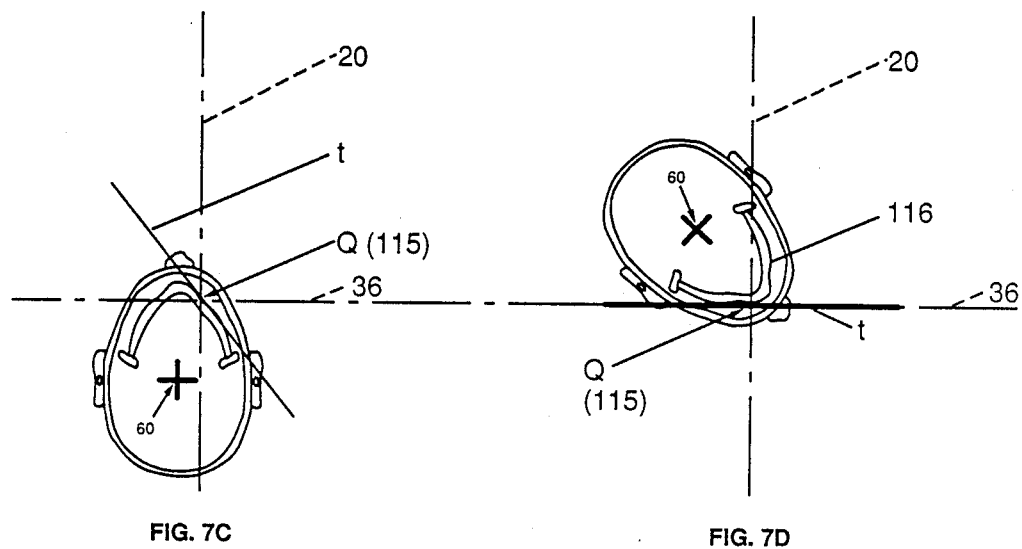
FIG. 7C   FIG. 7D
FIG. 7

How to Use the AxialTome MarkI Program

Step 1

Check to see that the mode select slider of the calculator is still set to [COMP] . (It should be.)

Step 2

Press the [ON] button and press the red [CL] (clear) button to clear the screen.

Step 3

Press the [PRO] button (just left of the green [COMP] key) once or twice until the screen displays the title:

01:     Implants
        Automatic

Step 4

Press the green [COMP] key to start the program.

Note: Pressing the red [CL] key will stop the program at any point and return the calculator to a clear screen.

Restart at Step 3.

FIG. 17A

Step 5

The screen shows:

> radius = ?

Use the numeric keypad and enter the radius (in millimeters) from the center of the head fixator to the pointer tip.

Press the green 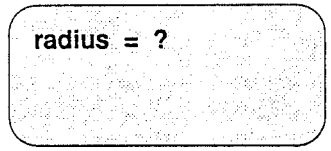 key.

Step 6

The screen shows:

> θ = ?

Use the numeric keypad and enter the pointer angle (in degrees) that is marked on the head fixator. (0 – 180°.)

Press the green 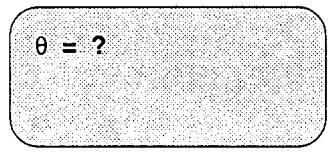 key.

Step 7

The screen will now look similar to this:

> newangl =
>          xx . xx

This is the newangle at which to set the head fixator.

Press the green 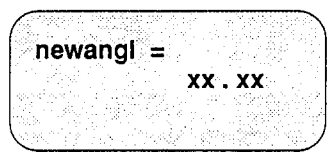 key.

FIG. 17B

Step 8

The screen now looks similar to this:

```
newangl =
            xx.xx
xstep =
            xx.xx
```

Xstep is the amount, in millimeters, to adjust the head fixator in the X direction.

Press the green 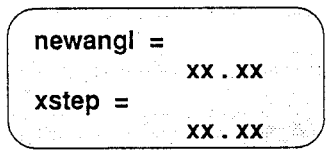 key.

Step 9

The screen will now look similar to this:

```
xstep =
            xx.xx
ystep =
            xx.xx
```

Ystep is the amount, in millimeters, to adjust the head fixator in the Y direction.

Step 10

Press the green 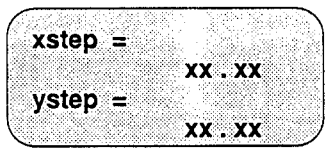 key to start again

OR

Press the red [CL] key to clear the screen

OR

Press the [OFF] button.

FIG. 17C

POSITIONING SYSTEM FOR A X-RAY TOMOGRAPHY

BACKGROUND OF THE INVENTION

The invention relates to an X-ray system for imaging the head and neck regions of the human anatomy including both static and tomographic modalities utilizing a limited output stationary anode X-ray tube system.

The system is designed with emphasis on installation in the offices of private practitioner, for example the dental profession, for utilization in projecting cranial images. Specifically, the images projected can be static images of the head and neck region of anatomy with emphasis on the tomographic projection of the temporomandibular joint and the maxilla-mandibular areas for the projection of osseus integrated implant sites. A specific aspect of this invention relates to the dental implant and to X-ray tomography as supporting the dental implant system in providing tomographic X-rays of selected implant sites, and is illustrative of one of the more difficult areas of anatomy to position for an accurate tomographic projection and is described here as an example. More particularly, this aspect of the invention is concerned with a positioning system, apparatus and method for precisely locating the patient in X-ray tomography such that the site of the anatomy of interest is at the correct position to provide an accurate tomographic X-ray projection.

Regarding the specific dental implant aspect of the invention the dental profession has been involved to an increasing degree with the osseus integrated implant system to facilitate dental prosthesis. In order to properly install an implant, an X-ray of the proposed site should be taken so that the dentist can investigate the adequacy of the osseus tissue to support an implant post at that site.

The X-ray of the mandible or maxilla should employ tomography in order to project the cross sectional area of the mandible or maxilla at the site. The site, i.e. the anatomy of interest, must be accurately positioned in the tomographic plane and in the central beam axis or isocenter of rotation of the X-ray in order to obtain the desired cross sectional image at the site.

X-ray tomography, as is well known, involves the constant movement of an X-ray source and photographic plate relative to the patient during exposure of the X-ray image. The X-ray source and plate rotate through an arc in which the X-ray beam continuously intersects a central axis or fulcrum plane axis at a focal point. The result is that all bone structure in front of and behind the plane of interest (i.e. on the sides toward and away from the plane of interest) are blurred and essentially do not appear in the image. Only that structure located at the fulcrum plane, i.e. a thin plane of bone structure, appears in the X-ray, so that the image is of a cross section of the bone tissue. The wider the arc of movement of the X-ray source during exposure, the thinner and more specific the depth of the resulting cross sectional image.

A problem for dentists practicing implant prosthesis has been the lack of a convenient, accurate, reliable and affordable source for obtaining X-ray tomographic sectional-plane images of proposed mandible or maxilla sites for implant. Generally the patient has been sent to a radiologist with instructions to investigate certain sites. The radiologist usually employs Computerized Axial Tomography ("CAT Scan") to project the necessary views. As a consequence, the procedure has involved an additional facility requiring separate scheduling and does not provide the immediacy of information desired, not to mention the radiation dosage and cost of the examination.

Previous to the present invention there has not been an accurate and convenient system that can be installed in a private office for correctly positioning a patient for X-ray tomographic imaging of potential dental implant sites such that in most cases, a single exposure and image can be taken for each location of interest.

SUMMARY OF THE INVENTION

In accordance with the present invention an apparatus, system and method are provided which solve the above described problems.

An instrument and system enable precise positioning of a selected site for X-ray tomography. The system and method involve the initial positioning of the patient accurately such that the head is positioned lateral to the X-ray central beam axis and centered on the fulcrum or tomographic cut plane with the patient immobilized utilizing a head fixating device. This fixating device includes a left and right adjustable pair of earposts that will locate on the entrance to the external auditory meatus and an adjustable rest that will position on the nasion. The earposts will reference the cranial anatomy to the X-ray central beam axis and the nasion will position the occlusal plane horizontally.

The fixator is supported on a three axis positioning stage to provide an orthogonal projection in the three cartesian coordinates. The fixator also pivots to provide an accurate angular position. The fixator further includes a pointer system that pivots on the fixator vertical axis of rotation with an adjustable radial pointer system that measures the distance from the center axis of rotation and the vertical distance from the X-ray central beam axis to the anatomical point of interest. The pointer is extendable to directly contact the site of interest.

The information thus obtained includes the polar coordinates of the site of interest. Through the use of a derived formula, calculations are made to convert this information to an angle and a set of X and Y coordinates that will position the anatomical site of interest correctly at isocenter (the point of intersection of the central beam X-ray axis, the fulcrum or tomographic cut plane and the vertical pivot axis of the fixator). The Z coordinate is read and adjusted directly.

To project the proposed site of an osseus integrated implant, the derived formula indicates the positioning of the mandible or maxilla such that the long axis of the curving bone is parallel to the X-ray central beam axis, with the fulcrum plane axis perpendicular to the mandibular or maxillary arch angle of tangency.

The clinician or technician is thus enabled to take the measured information, convert the data to the calculated position, adjust the apparatus and position the patient, and then finally expose the radiograph. After processing, the clinician has a projection of the proposed site for implant placement or a post installation projection for positioning assessment.

It is therefore among the objects of the present invention to improve the efficiency and accuracy of cranial imaging, and particularly the dental implant prothesis system. This will be done by virtue of an accurate anatomical positioning apparatus that will afford the clinician a reliable, moderately costing system which can be installed in a private office environment. The apparatus is also capable of additional tomographic and static methodology to project cranial images.

Other and further objectives of the present invention will be apparent from the following description and claims and are illustrated in the accompanying drawings. These drawings, by way of illustration, show preferred embodiments of the present invention and the principles thereof and what are now considered to be the best modes contemplated for applying these principles. Other embodiments of the invention embodying the same or equivalent principles may be used and structural changes may be made as desired by those skilled in the art without departing from the present invention and the purview of the appended claims.

DESCRIPTION OF THE DRAWINGS

FIGS. 6A and 6B are side and frontal elevation views of a pointer device forming a part of the head fixator.

FIGS. 7A, 7B, 7C and 7D illustrate the patient in a reference position for measuring the location of a site of interest on the patient for X-ray tomography (FIG. 7A). The desired final position of the patient with a tangent to the mandibular arch at the site parallel to the tomography plane (FIG. 7D), and problems in arriving at this desired position (FIGS. 7B and 7C).

FIG. 14B illustrates the tomographic plane.

FIGS. 17A, 17B and 17C are an explanation of using the program as it is to be incorporated in the operating manual for the tomographic device.

DESCRIPTION OF PREFERRED EMBODIMENTS

Figure 1:
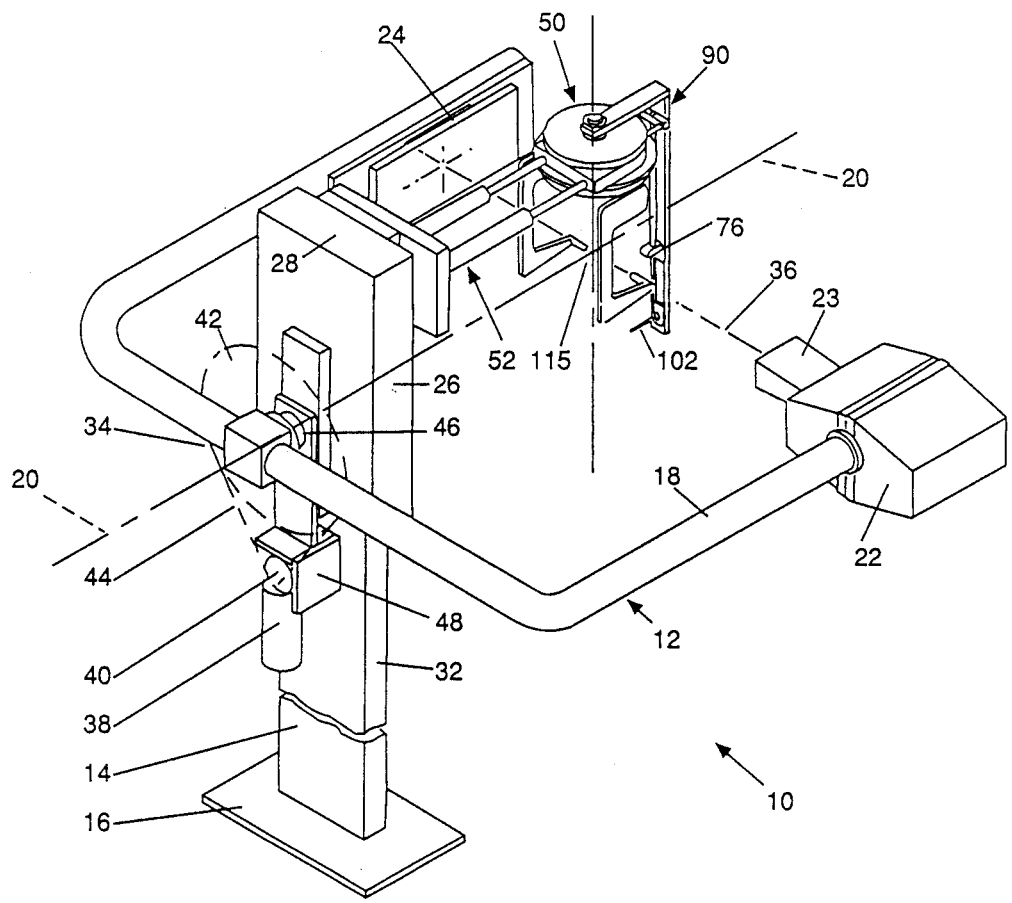
FIG. 1 is a rear perspective view showing an X-ray tomography apparatus including a positioning device and system according to the invention.
Figure 2:
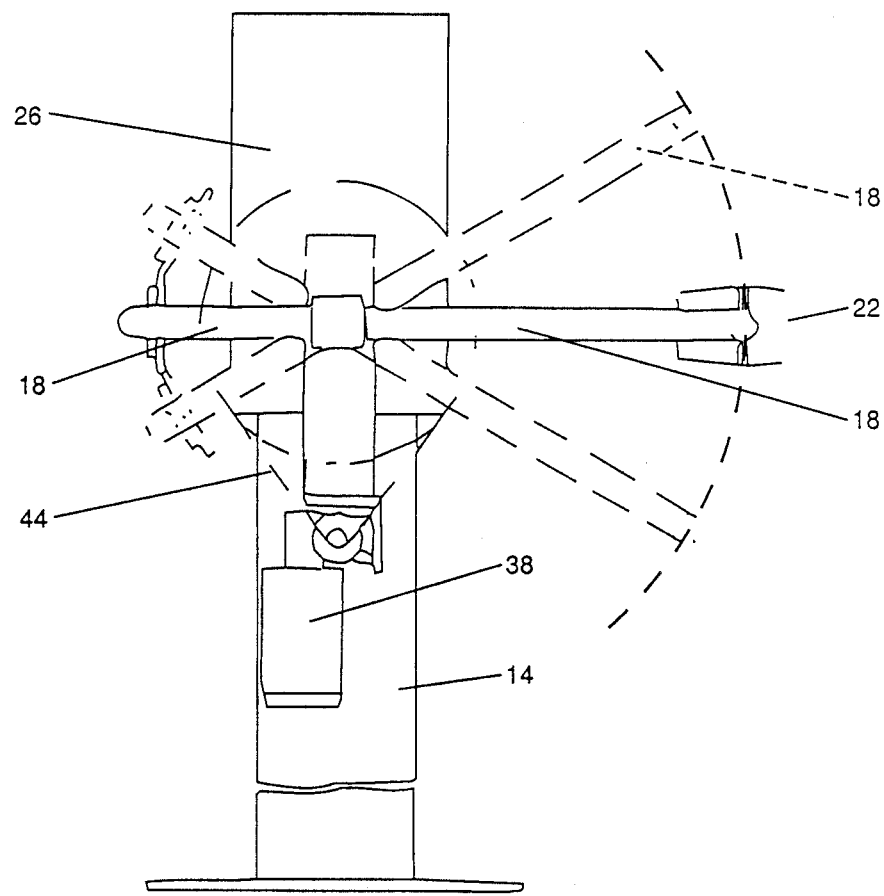
FIG. 2 is a rear view of the apparatus, indicating an arc of movement of an X-ray source, in accordance with the tomography process.

In the drawings, FIGS. and 2 show an apparatus 10 constructed in accordance with the principles of the present invention.

The system and apparatus 10 include a tomographic X-ray assembly generally identified by the reference number 12 and including a column 14 with a base or floor stand 16, an arm or spar 18 which is rotatable about a horizontal axis 20, an X-ray source comprising a tube head 22 at one end of the spar 18 and an X-ray film cassette holder 24 at the other end of the spar 18. The column 14 supports a carriage 26 which is counterbalanced with negator springs mounted on top of the column (not shown). Rollers (not shown) are mounted on the carriage to provide vertical linear movement The carriage 26, being vertically slidable, is adjustable to a patient's standing (or sitting) height. The carriage actually supports the spar 18 with the X-ray tube 22 and X-ray film cassette holder 24, so that the X-ray apparatus rises and falls along with the carriage. A hand brake (not shown) is used to fix the carriage in a stationary position.

A spar drive mechanism shown generally at 34 rotates the spar about the horizontal axis 20, which is the fulcrum plane axis of the tomography procedure. The axis 20 is thus always intersected by an X-ray beam center axis 36 passing from the tube head 22 to the X-ray film cassette holder 24. A vertical plane in which all X-ray center axes 36 lie while the spar rotates is referred to herein as the X-ray. Another vertical plane, referred to herein as the tomographic plane, is the cross section plane in which the tomographic X-ray projection is taken, and is illustrated in FIG. As shown in FIG. 1, a beam limiter 23 on the tube head limits the size of the emerging X-ray beam.

The spar 18 is driven by a DCPM gear motor 38 through a sprocket and chain assembly 40, 42 and 44. A spar support shaft 46 is mounted on the pivot axis 20 and supported by the carriage 26. Motion limits on rotation of the spar 18 are controlled by limit switches (not shown) mounted on the larger sprocket 42.

The spar drive mechanism 34, in one preferred embodiment, may be set up to rotate the spar 18 in a 60° arc, 30° above and 30° below the horizontal plane.

Also supported on the vertically slidable carriage 26 is a head fixator assembly 50. It includes an orthogonal X, Y and Z positioning mechanism, as further explained below with reference to FIG. 3. With the X, Y and Z positioning mechanism set, the head fixator assembly 50 is movable up and down along with the carriage 26 and the X-ray supporting spar 18.

As is well known in tomography, the spar with the x-ray source 22 and X-ray film cassette holder 24 is rotated continuously while an X-ray exposure is made of a site on a patient. In such tomography, the patient is immobilized using a head fixator somewhat similar to the head fixator 50, not including the features of the present invention.

The cassette holder 24 supports an X-ray film cassette at the prescribed focal-film distance from the X-ray source 22.

Figure 3:
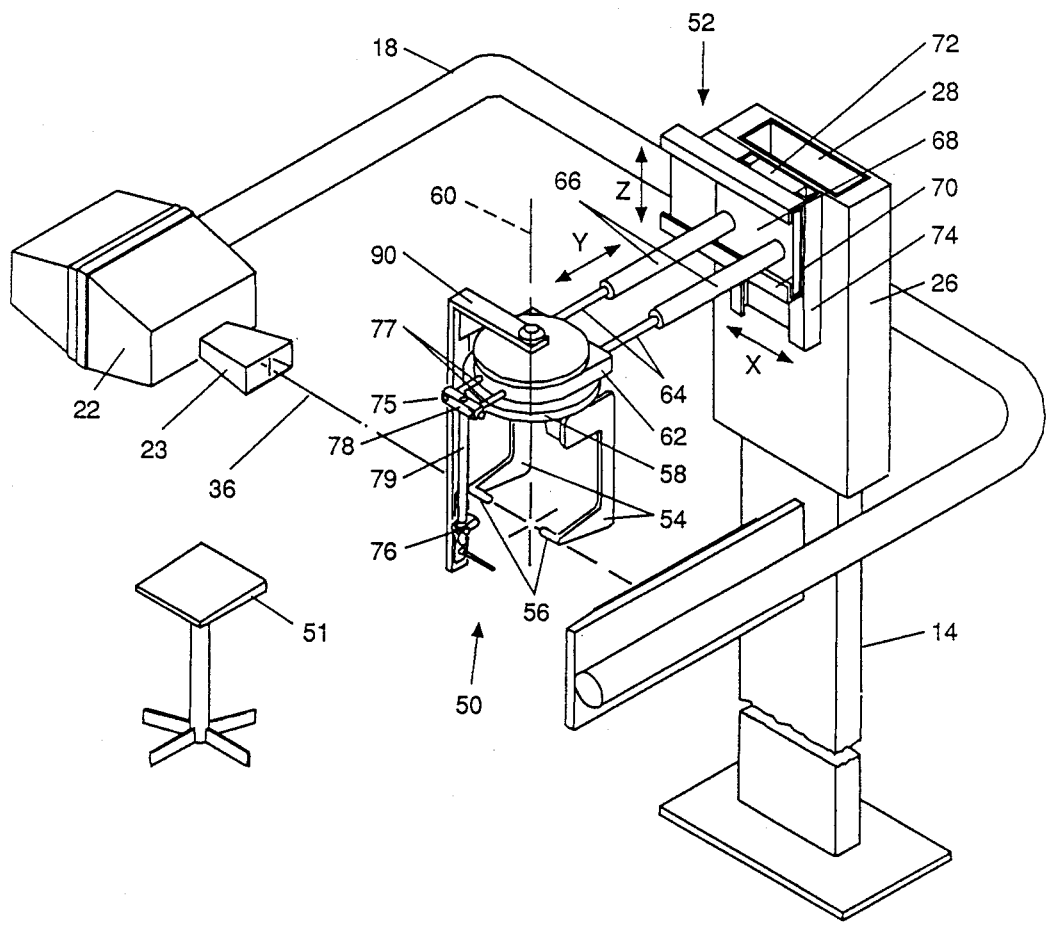
FIG. 3 is a frontal perspective view showing a portion of the apparatus and system of FIG. 1 and showing the X-ray source aligned along the transmeatal line of a cephalostat or head fixator device of the apparatus including the nasion stabilizing device and pointer assembly.

FIG. 3 shows a portion of the apparatus 10, particularly the head fixator mechanism 50 and the associated X, Y and Z positioning mechanism 52, in greater detail. FIG. 3 indicates schematically a pedestal mounted X-ray control 50 of the tomography machine. The X-ray control 51, preferably connected by an electrical cable (not shown) through the column 14 and the spar 18 to the tube head 22, enables the operator to face the patient and to view the patient's position before activating the X-ray and spar drive.

Figure 5:
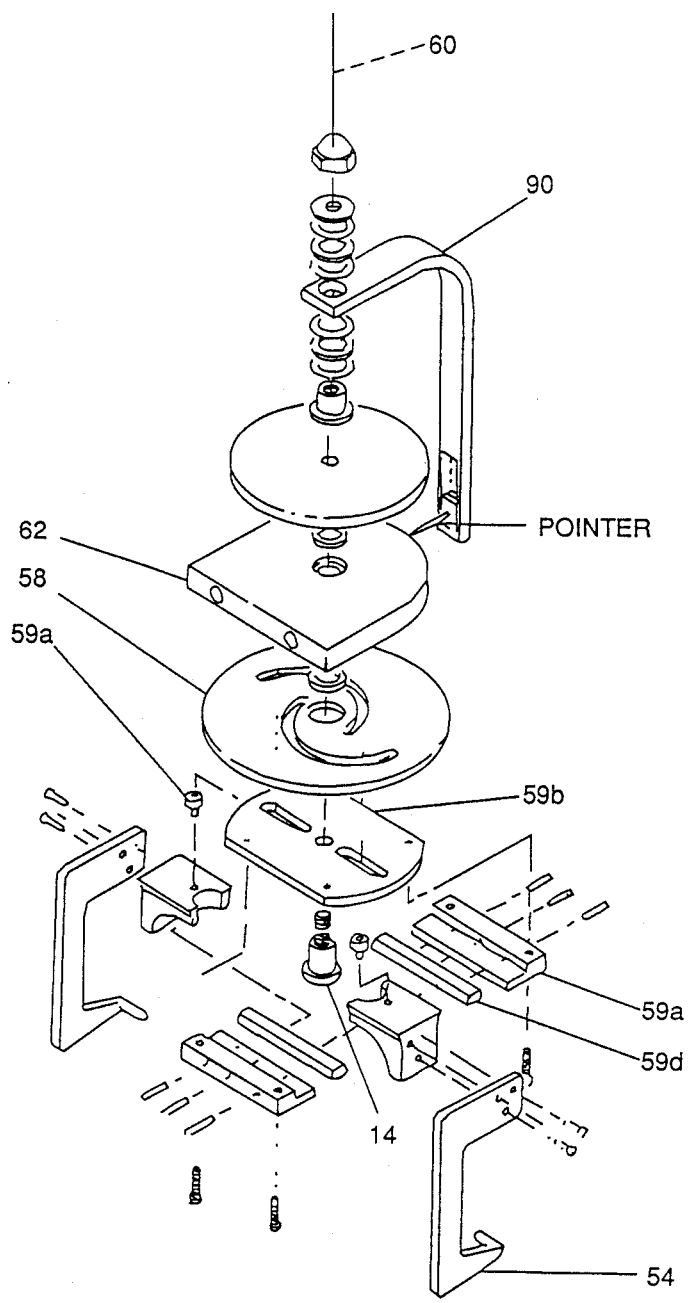
FIG. 5 is an exploded view in perspective indicating components and assembly of the head fixator device.

The head fixator apparatus, shown in greater detail in FIG. 5, includes a pair of earpost brackets 54 each of which has a round-tipped earpost 56. As in previous head fixator devices, these are used to immobilize the head. The brackets are supported on sliding blocks (for adjustable separation) that are positioned for linear movement with respect to a rotating cam plate 58 and Camrol bearing 59 in conjunction with a guide plate 59b to provide an equidistant telescoping movement. The sliding blocks are slidably received within the slide members 59c in a closely fitting connection controlled by adjustable gibs 59d which admits very little lateral movement and maintains the earpost bracket and earpost in a predetermined position along the horizontal X-ray beam axis 36 (FIGS. 1 & 3).

The brackets 54 are connected to a rotation assembly 58 which enables rotation of the device about a vertical axis 60 as indicated in the drawing. As shown particularly in FIG. 3, this apparatus is supported on a frame member 62 which is connected to the ends of a pair of X-axis adjustment rods 64. These rods are telescopically and slidably received within support cylinders 66, in a closely fitting connection which admits very little lateral movement.

The cylinders 66 extend from a slide block 68 which fits closely within a receiving channel 70 to permit accurate left-to-right or X axis adjustment.

The support channel 70 in turn is connected to a Z-axis support block 72 which is vertically slidable within a Z-axis support channel 74 mounted to the carriage 26. This provides for Z-axis or up-and-down movement of the head fixator device with respect to the carriage and the mid-level of the X-ray beam 36. As discussed previously above, the rotatable spar 18 with the X-ray tube head 22 is connected to and moveable up add down along with the carriage 26. The Z-axis movement 72, 74 provides for Z-axis movement relative to the carriage 26.

The Z-axis direction of motion of the head fixator assembly 50 is counterbalanced with a negator spring assembly (not shown). All three motions (X, Y and Z) are fixed with hand brake assemblies (not shown) when the correct position has been obtained.

In this way, the positioning assembly 52 associated with the head fixator assembly allows for precise positioning of the cranial anatomy at the intersection of the vertical or X-ray plane containing all central X-ray beam axes 36) and the spar rotation/isocenter axis 20.

FIG. 3 further includes a nasion stabilizer device 75 which is secured to the frame member 62 of the head fixator. This enables the engagement of the patient's nasion (the bridge of the nose) by a nasion contacting element 76, to prevent any substantial rotational movement of the patient's head about the axis 36 or transmeatal line 84 (see FIG. 4) thereby stabilizing the position of the head with respect to all movements.

As illustrated, the nasion stabilizer assembly 75 is supported on rigid posts 77 which are fixed relative to the frame member 62. An upper bracket 78 permits in/out adjustment movement of the nasion engaging member 76, by sliding on the posts 77 when the bracket is loosened. In addition, the nasion engaging element 76, which is secured to a vertical rod 79, is slidable vertically on this rod in order to match the height of the element 76 to the particular patient's nasion.

Figure 4:
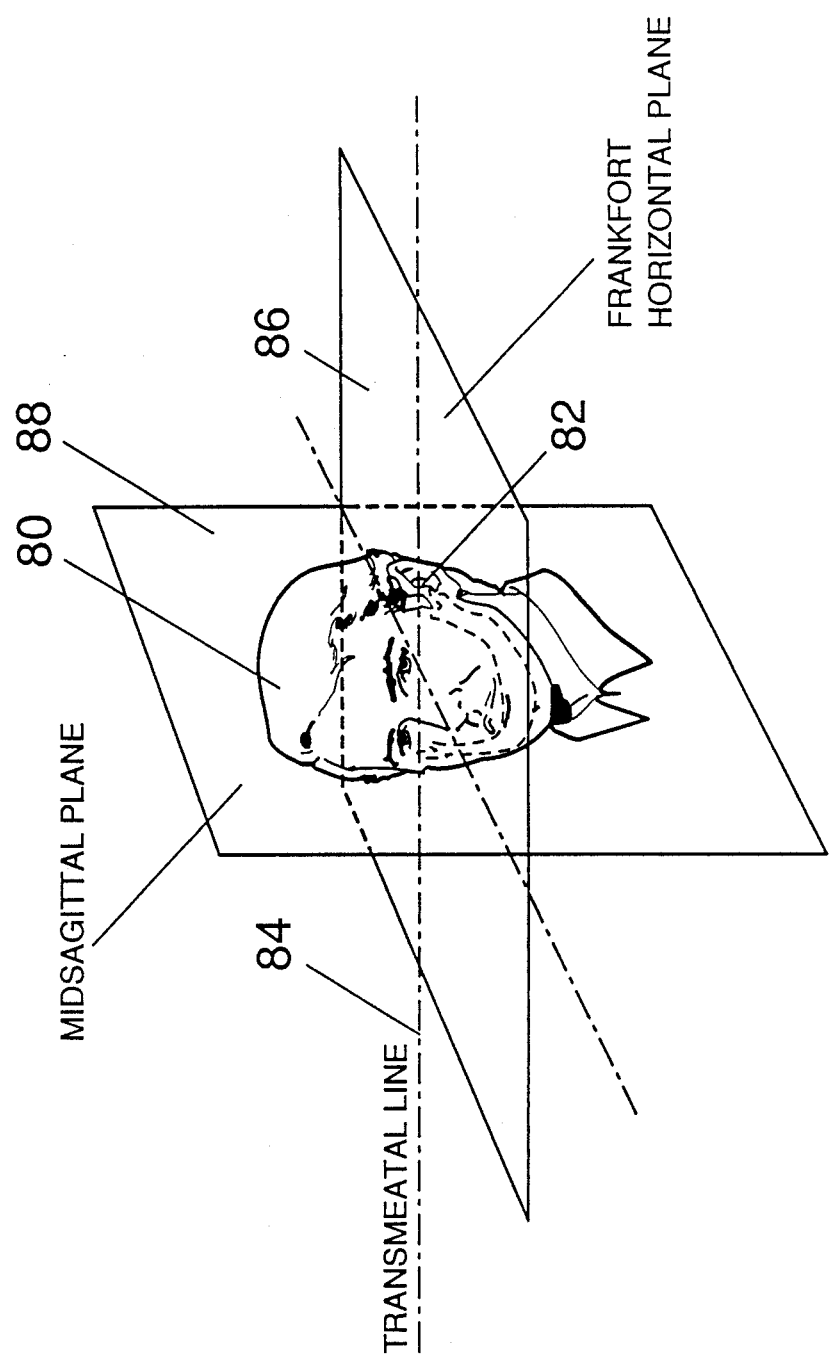
FIG. 4 is a schematic view showing a patient's head and illustrating the midsagittal plane of the head as well as the transmeatal line and the Frankfort Horizontal plane, which are relevant to the method, apparatus and system of the invention.

FIG. 4 shows several reference planes and lines of the human cranium as they are defined medically. These planes and lines are useful as references in aligning the head 80 of a patient and in the discussion of the invention which follows.

The ear cavities 82 define the external auditory meatus, with a horizontal line passing through these points 82 defined as the transmeatal line 84. A horizontal plane passing through the transmeatal line and through the floor of the orbit is defined as the Frankfort horizontal plane 86. A vertical plane 88 passing through the center and bisecting the head including the nose is called the midsagittal plane. Another horizontal plane is the plane that intersects the occlusal surfaces of the teeth and is called the occlusal plane (not shown in FIG. 4).

In accordance with the present invention, some of these planes and lines are used to reference the position of the patient in the X-ray tomography system and to define and determine a measured correction of the patient's cranial position in X, Y and Z coordinates and in rotational position about a vertical axis.

FIGS. 6A and 6B show side and front end views of a pointer assembly 90 which forms an important part of the present invention. The pointer assembly 90, as shown in FIGS. 1 and 3, is connected to the head fixator or cephalostat assembly 50 and is pivotable about the vertical axis 60 shown in FIG. 3, relative to the ear posts 56 and other structure of the head fixator.

The pointer assembly 90 includes a pivotable arm 92 having a horizontal portion 94 and a depending vertical portion 96. The arm is pivoted about the axis 60 via a bolt 98 and bushing 100 shown in FIG. 6A. It is firmly held by the bolt 98 so that it may be pivoted about the axis 60 but with very little tolerance for movement in other directions.

Figure 6C:
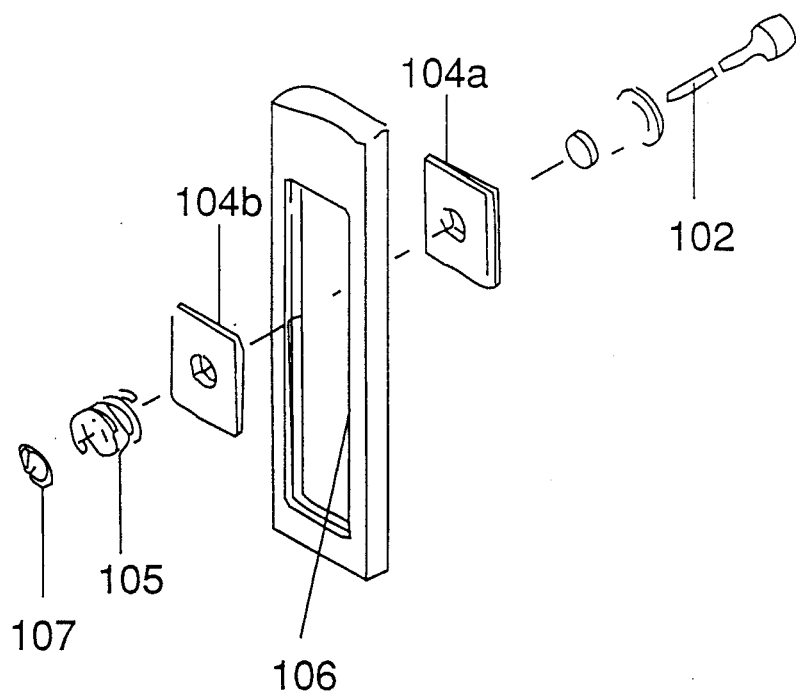
FIG. 6C is an exploded view showing a part of the pointer assembly.

A pointer 102 connected in the vertical portion 96 of the arm 92 is capable of movement in two directions: up and down in the Z direction via a slidable bushing 104 which slides preferably in a keyed slot 106 as shown in FIG. 6B and in exploded view in FIG. 6C; and in a radial direction R shown in FIG. 6A via a movement of the pointer 102 in and out of a cylindrical slide fitting 108 affixed to the slide bushing 104. The direction R is radial with respect to the vertical pivot axis 60, so that with the dimensions of the pointer assembly 90 precisely known and referenced with respect to the axis 60 and the isocenter axis 20 (FIG. 1), the pointer 102 can identify the location of any point in space contacted by its tip 110. A scale such as shown at 112 is included for the Z direction measurement, and a similar scale 113 is included on the pointer rod 102 for measurement in the R direction.

FIG. 6C shows one preferred construction for the Z-axis slide assembly of the pointer assembly. The pointer 11 is supported with a tension fit in pointer bushing 12 that is supported by the rear slide 104a and front slide 104b that have a mating fit with the 10 slide aperture 106 on the pointer body 102. A spring 105 and a retaining ring 107 provide the means to mechanically affix the front and rear slides to the pointer body under tension. The Z axis scale (not shown) indicates the distance from the transmeatal line to the axis of the pointer 102 (FIG. 6A).

It can be seen that from the measurement of an angle of deviation of the pointer rod 102 in either direction from the midsagittal plane or isocenter axis 20 (the straight ahead position shown in FIG. 1), and a radial distance representing extension of the pointer rod 102 in the radial direction R, the position of the pointer 110 in space can be defined relative to the isocenter of the vertical plane of all X-ray axes, within which the axis 36 lies (FIG. 1). This assumes that the position of the head fixator assembly 50 is known, relative to its permitted translations along X, Y and Z axes. This position is precisely known, since all of the X, Y and Z translations are fully calibrated.

Further, in preferred embodiments of the invention the head fixator assembly is positioned at a point defined as 0,0 on all translational axes, wherein the fixator is aimed straight ahead such that the midsagittal plane is along the isocenter axis 20 and the ear posts 56 are along the X-ray beam center axis 36 when the spar 18 is horizontal, as shown in FIG. 1. The zero rotational position of the pointer assembly 90 is at the midsagittal plane and the pointer rod 102 can be calibrated such that at a theoretical zero position, the tip 110 would be assumed to be precisely at the vertical rotational axis 60, even though the pointer tip in reality would never be required to reach this far inward.

It is therefore clear that with such an angle and radial distance known, i.e. polar coordinates of a point known, X, Y and Z cartesian coordinates of the same point in space can be calculated. With such coordinates calculated, adjustments can be made to the position of the head fixator assembly, using the X, Y and Z translational mechanisms described above to reposition the patient such that a site of interest measured with the pointer tip 110 can be relocated precisely at the intersection 115 of the isocenter axis 20 and the horizontal X-ray center axis 36 shown in FIG. 1. The Z (height) adjustment is relatively simple, as measured by the pointer rod 102.

However, FIGS. 7A through 7D illustrate that another requirement of implant X-ray tomography makes the X and Y position problem somewhat more complex. This is the requirement that, for accurate mandible or maxilla cross-sectional X-rays, a tangent to the mandibular arch must be substantially parallel to the vertical plane of all X-Ray axes seen in the plan views of 7A-7D, as the X-ray center axis 36.

In FIGS. 7A-7D, the exterior of the mandibular arch is represented at 116. The mandibular arch 116 has a curvature which is not arcuate and clearly not with a center located at the vertical axis 60 of rotation of the head fixator assembly 50. The cross-sectional X-ray obtained by tomography is intended to show as closely as possible a perpendicular cut through the mandibular or maxillary bone structure; thus the mandibular arch should be as closely as possible tangent to the plane 36.

FIG. 7A shows a patient's head 118 held in the 00 position as discussed above and as the equipment is shown in FIG. 1. This is a reference position from which to take measurements to the site of interest Q. The pointer rod 102 and arm 92 are moved to a rotational position and to a rod extension position such that the pointer tip 110 substantially contacts the site of interest, as indicated in FIG. 7A by the radial arrow pointing to the site Q. From the obtained polar coordinates, the needed X and Y translational shift of position and the angular shift of position of the head fixator assembly 50 can be calculated so as to put the site precisely at the isocenter axis/vertical plane intersection 115. This is shown in FIG. 7B, wherein the head 118 has been rotated through an angle sufficient to move the site Q to the tomographic plane 36, and the head fixator apparatus 50 has been moved through an X-direction translation so that the site Q is precisely at the intersection of the plane 36 and the isocenter axis 20.

FIG. 7C also shows that the position of the site Q can be relocated to the isocenter/tomographic plane in section 115 through X and Y translations only, with no rotation. However, in both cases the tangent t to the mandibular arch at the site Q is not parallel to the tomographic plane 36, as is required. The patient must instead be oriented as shown in FIG. 7D, with the mandibular arch properly tangential to the plane 36 at the site Q, with the site also precisely at the isocenter/plane intersection 115. This requires a calculation involving the expected curvature of the patient's mandibular arch at the particular site in question and a further rotation of the head fixator about the vertical axis 60, as well as further X and Y adjustments.

The calculation of the correct rotational orientation and X and Y position of the patient is relatively complex, and the solution to this problem is an important feature of the invention.

Figure 15:
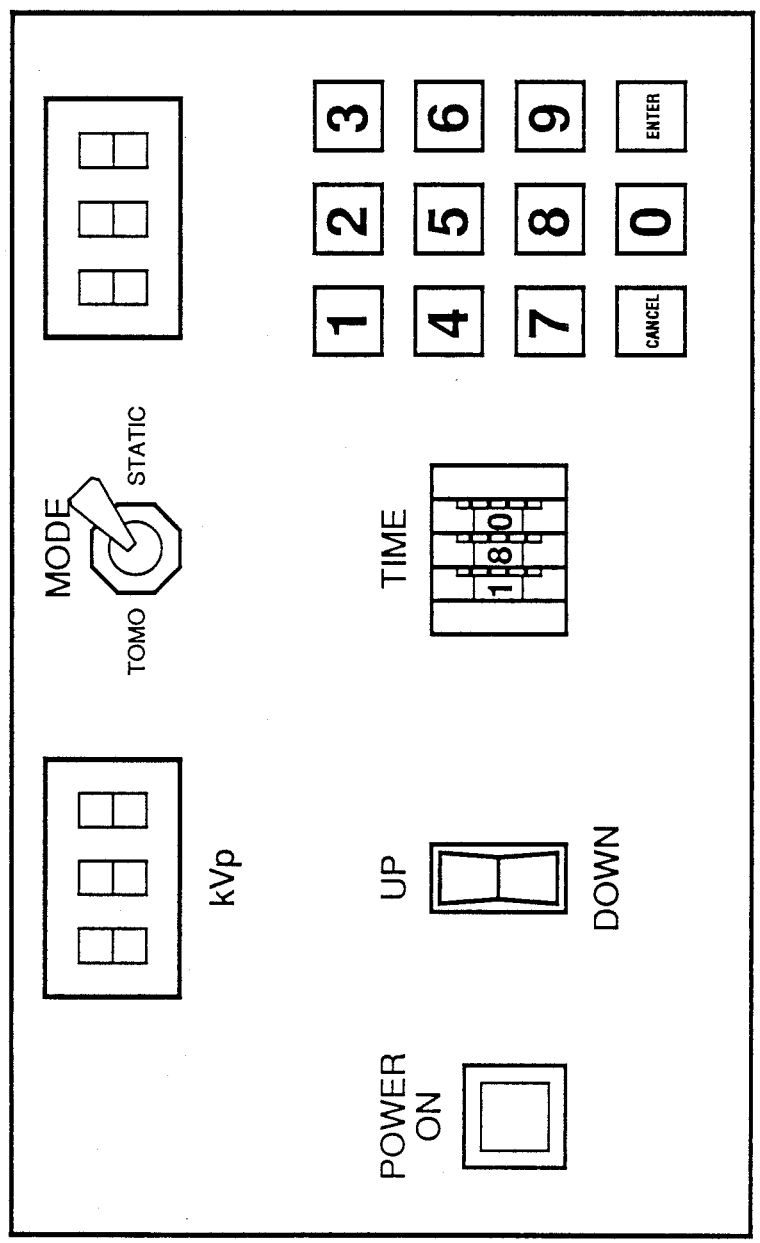
FIG. 15 is a schematic view of the tomographic unit control pedestal control panel.
Figure 16:
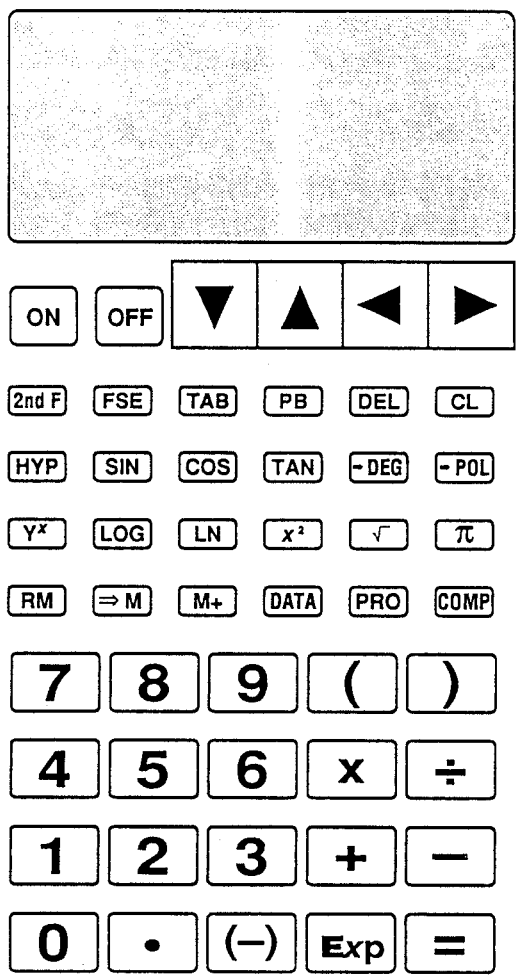
FIG. 16 is a schematic view of the Sharp EL-5200 Super Scientific Calculator's main keyboard.

In accordance with the invention, as further described below, formulae were developed for several different classifications of mandibular arch shapes from digitizing the mandibular arches of a large collection of human skulls. In the method of the invention the formulae are used as part of a procedure for converting the polar coordinates (radius, angle) derived from the pointer assembly 90 to cartesian coordinates (X, Y) which not only place the mandibular site of interest at isocenter in the plane 36, but which also align the patient such that the tangent to the mandibular curve is parallel to the plane 36, i.e. perpendicular to the isocenter axis of rotation 20 in the tomograph. Each of these formulae is programmed into a small hand-held computer/calculator as indicated in FIG. 16, for ease of use of the procedure. In one embodiment of the invention, the computer can also be mounted on the machine itself within the X-ray control as indicated in FIG. 15.

The following discussion shows mathematical calculations which can be made in accordance with the invention to convert from the measured polar coordinates to adjusted cartesian coordinates which place the mandible at isocenter with the curve tangent parallel to the plane 36 of X-ray centers. These calculations employ the use of fourth order polynomials to mathematically represent the curvature of the mandibular arch for the patient.

Figure 8:
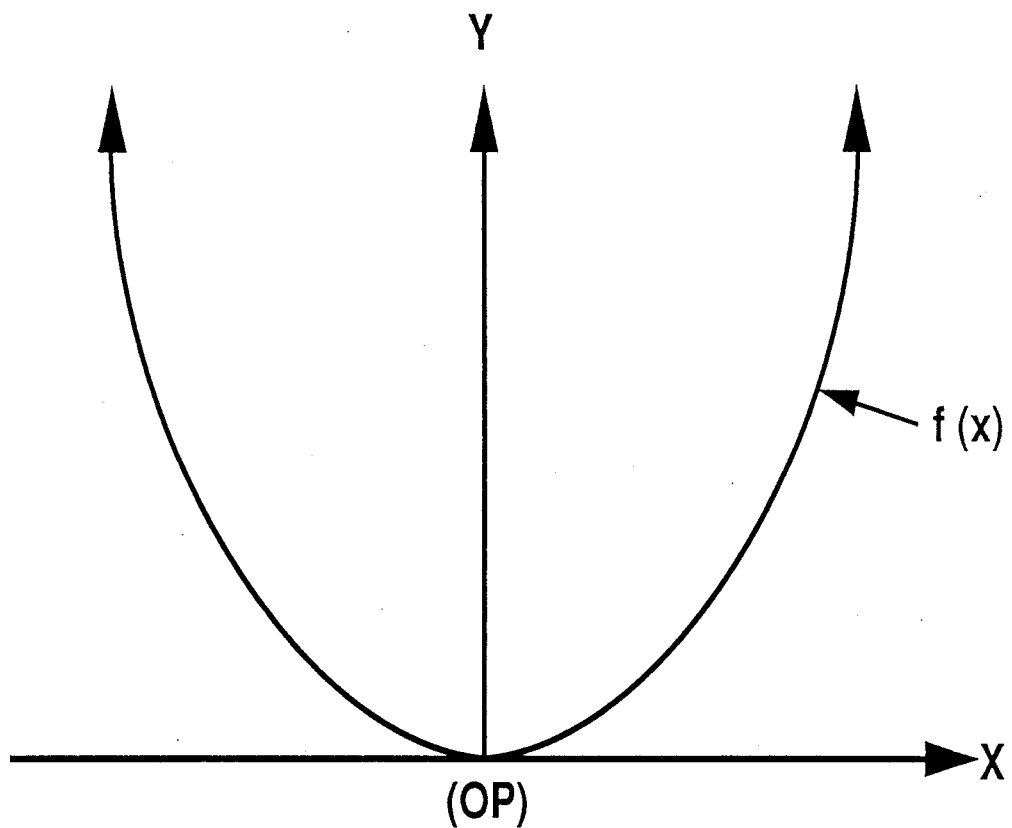
FIGS. 8 through 12 are diagrams showing derivation of the needed adjustments to reach the final position of FIG. 7D.

It has been found that the mandibular curve for the majority of adult patients can be expressed by one formula (see curve of FIG. 8). It should be understood that the calculations which follow involve a general case, and that the constant coefficients which the polynomial employs may be adjusted to provide a more accurate representation on a patient by patient basis. A programmable calculator can easily implement the needed calculations. An example of such a calculator is the Sharp EL-5200 Super Scientific.

Referring to FIG. 8, the mathematical function that describes the curve of the mandible horizontally (i.e. parallel to the Frankfort plane) can be defined as f(x) in terms of:

$$y = f(x) = A + Bx + Cx^2 + Dx^3 + Ex^4$$

where A, B, C, D and E are constant coefficients.

The slope of any point on this curve can be defined by taking the first derivative of f(x).

$$\text{Slope} = f'(x) = B + (2C)x + (3D)x^2 + (4E)x^3$$

Figure 9:
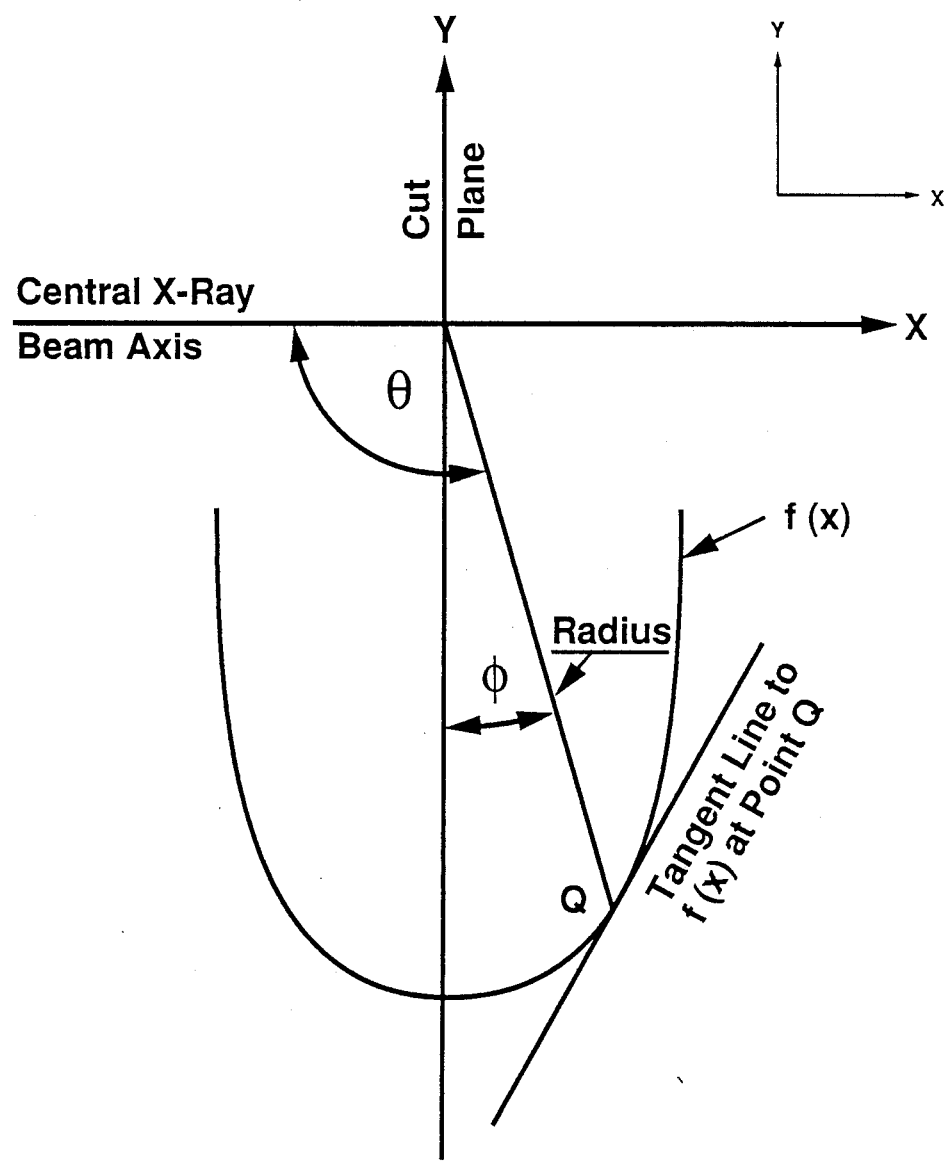

If the radius (in millimeters) and the angle Θ (in degrees) can be provided by the pointer system, as illustrated in FIG. 9, we can define the cartesian X coordinate of point "Q" by:

$$x_1 = \text{Radius} * \text{SIN}(\Theta - 90°)$$

And, since the function f'(x) for the curve is known, the slope at point Q can be found by evaluation of f'(x) at $x_1$:

$$\text{Slope}_Q = f'(x_1) = B + [(2C)*x_1] + [(3D)*x_1^2] + [(4E)*x_1^3]$$

Figure 10:
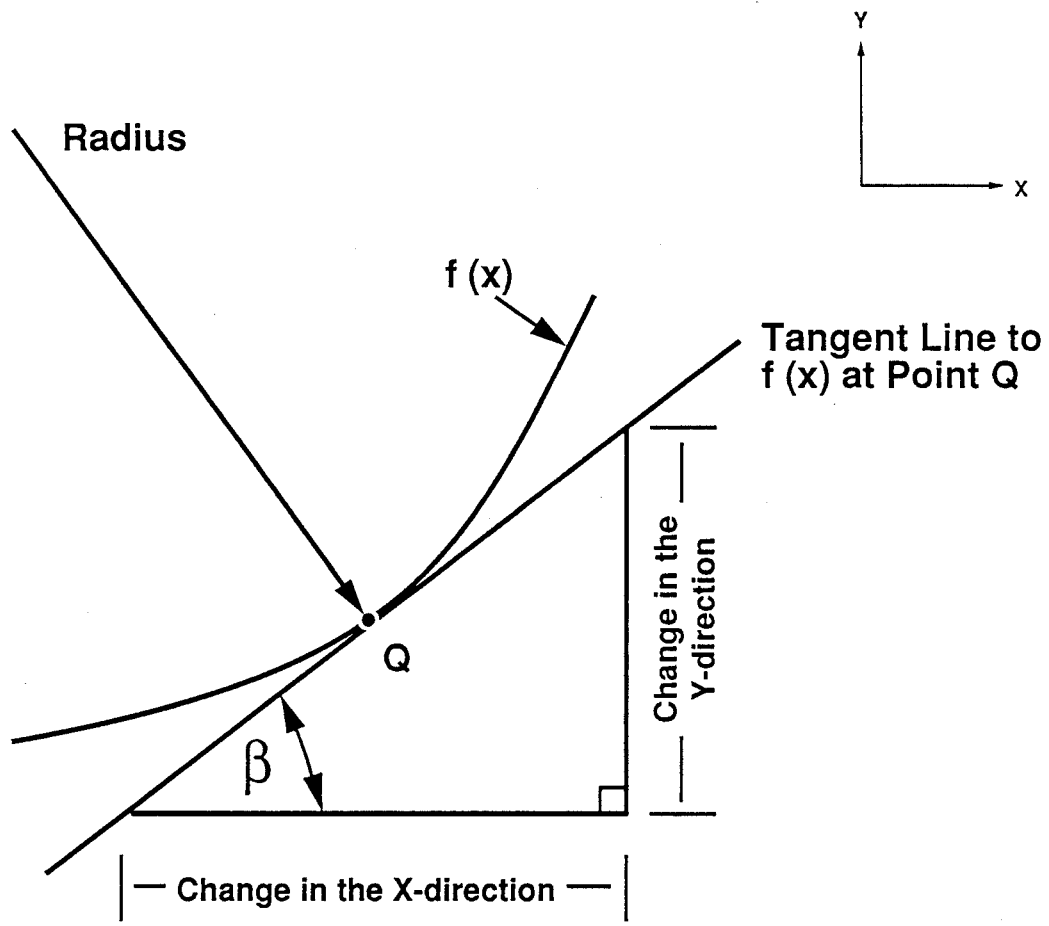

A closer inspection of point Q is indicated in FIG. 10. $\text{Slope}_Q$ defines the slope (change in Y direction / change in X direction) of a line tangent to point Q. The angle β can be found by:

$$\beta = \text{TAN}^{-1}(\text{Slope}_Q)$$

It is desired to align the tangent line to f(x) at point Q coincidentally with the central X-ray beam axis. The next step is to adjust the cephalometer angle so that the tangent is parallel to central X-ray beam axis (see FIG. 11). The new cephalometer setting is calculated by:

$$\text{Newangle} = 90° - \beta$$

Figure 12:
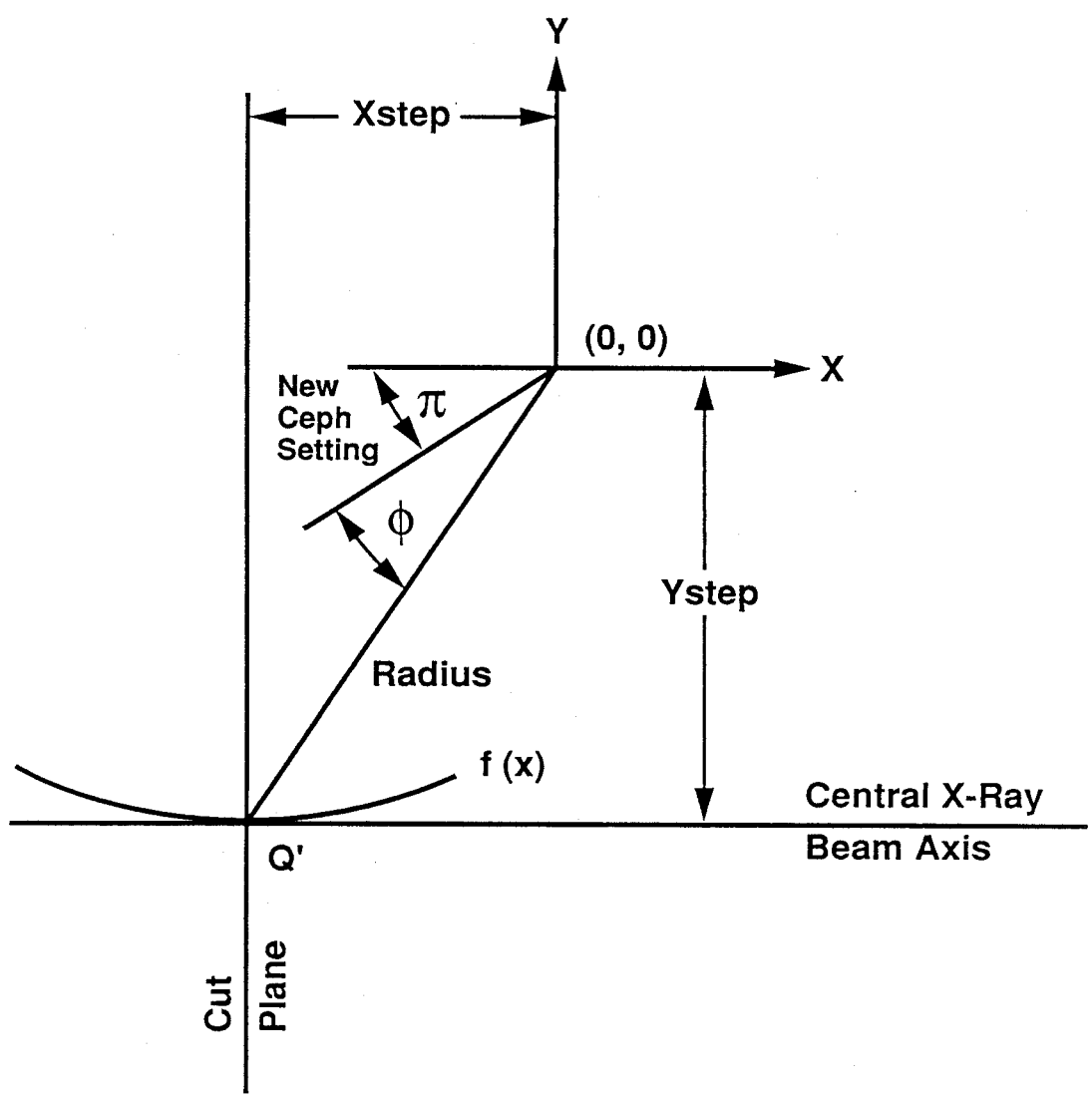

The final step is to translate the new point Q' to the intersection of the central X-ray beam axis and the cut or tomographic plane (see FIG. 12). This is done by moving the cephalometer XSTEP and YSTEP from its (0,0) position, where:

$$\text{XSTEP} = \text{Radius} * \text{COS}(\Theta - \beta)$$

$$\text{YSTEP} = \text{Radius} * \text{SIN}(\Theta - \beta)$$

This is illustrated in the step text diagrams of FIGS. 17A, 17B 7C. In summary, the steps are:
1. Input the radius (in millimeters) from (0,0) on the head fixator to the programmed calculator.
2. Input the angle θ (in degrees) from the midsagittal plane to the programmed calculator.
3. Calculate:

$$x_1 = \text{Radius} * \text{SIN}(\theta - 90°)$$

4. Using $x_1$, evaluate the slope $$\text{Slope}_Q = f'(x_1) = B + [(2C)*x_1] + [(3D)*x_1^2] + [(4E)*x_1^3]$$

5. Calculate the angle β from the slope:

$$\beta = \text{TAN}^{-1}(\text{Slope}_Q)$$

7. Compute the new angle setting for the head fixator:

$$\text{Newangle} = 90° - \beta \text{ (value in degrees)}$$

8. Compute the required change in the x direction:

$$\text{XSTEP} = \text{Radius} * \text{COS}(\Theta - \beta) \text{ (millimeters)}$$

9. Compute the required change in the y direction:

$$\text{YSTEP} = \text{Radius} * \text{SIN}(\Theta - \beta) \text{ (millimeters)}$$

Figure 11:
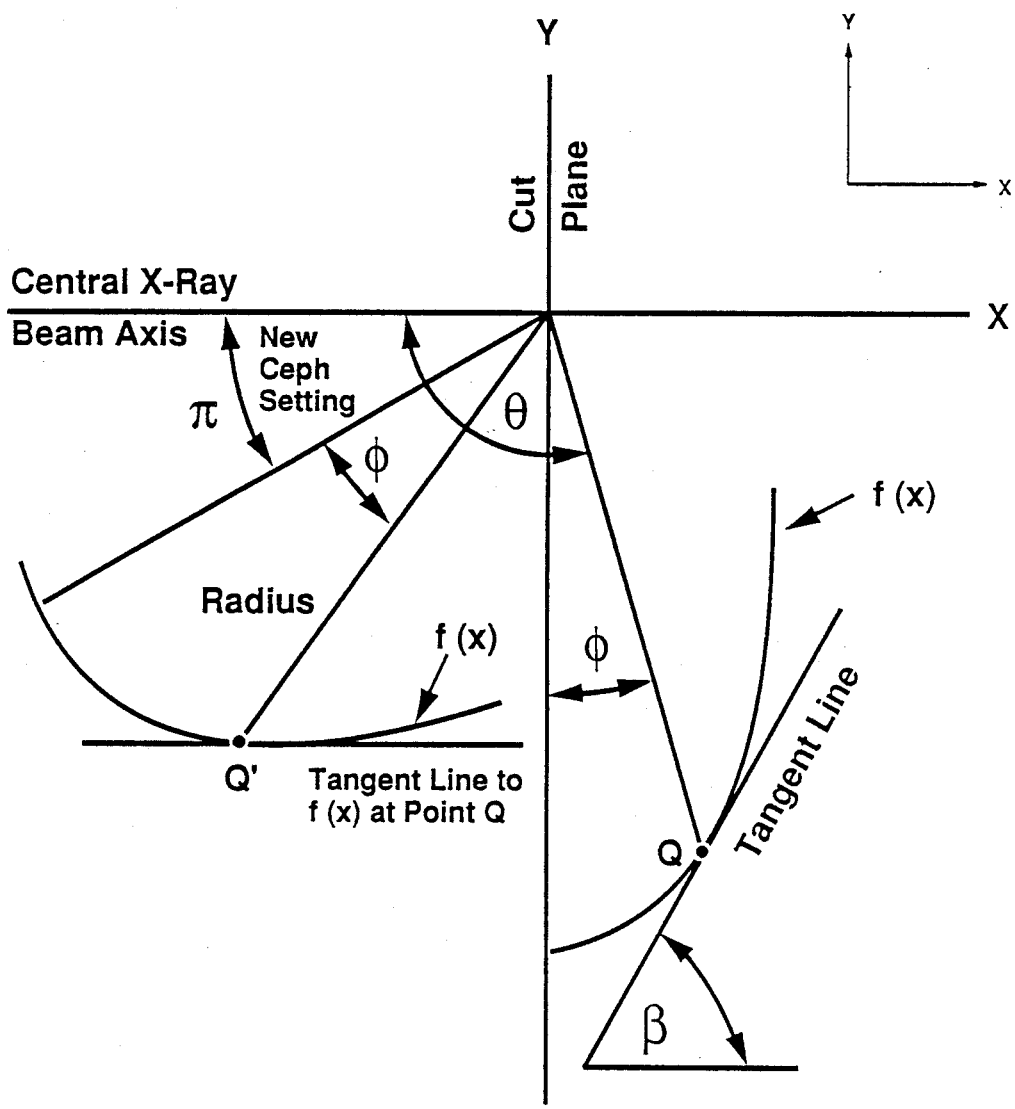

The operator would then adjust the head fixator from its zeroed position (fixator zero is aligned at 90°) to Newangle. The head fixator would then be moved in the X direction by the amount XSTEP, and in the Y direction by the amount YSTEP. The Newangle is represented in FIGS. 11 and 12 as π.

Figure 13:
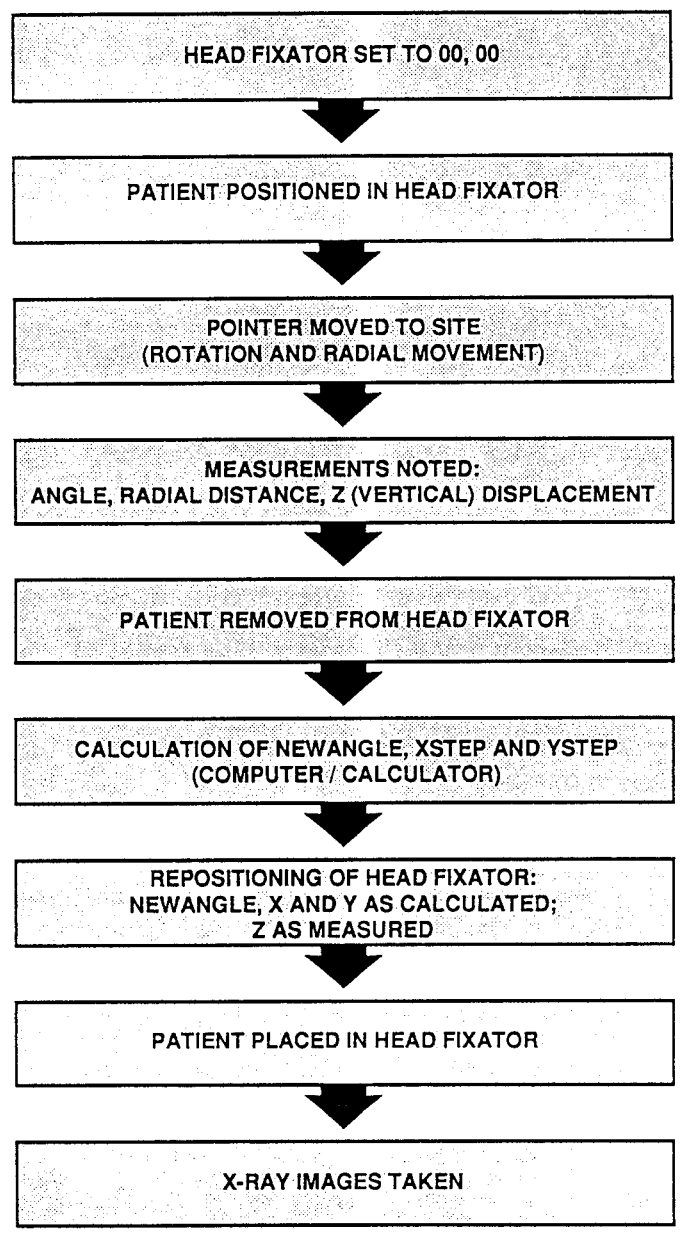
FIG. 13 is a simplified flow chart indicating steps in the method of the invention, in arriving at the correct positioning of the patient for X-ray tomography of a potential implant site.

The use of the apparatus and system of the invention is schematically represented in the block diagram of FIG. 13, and is as follows:

The patient is to be placed in the head fixator positioned so that the midsagittal plane is parallel with the film plane. The fixator is indexed at zero position (90°) and the coordinates read 00,00. A spint has been fabricated such that the implant site is located with a steel 5 millimeter ball held above the edentulous ridge. The pointer is positioned to indicate the distance from the center of the head fixator rotation and the angle referenced to the central beam axis. The angle and distance are noted on a work sheet. Additional sites are located at this time.

The radial distance (R) and the angle (Θ) are entered into the programmed calculator. The Newangle, XSTEP and YSTEP are then calculated. The Z distance is read from the pointer.

The patient is removed from the fixator and the fixator is positioned as calculated. The patient is again placed in the fixator and positioned. The X-ray is taken and marked for correlation with the site and calculation.

While we have illustrated and described the preferred embodiments of our invention, it is to be understood that these are capable of variation and modification and we therefore do not wish to be limited to the precise details set forth, but desire to avail ourselves of such changes and alterations as fall within the purview of the following claims.

We claim:

1. A system for positioning the head of a patient accurately for tomographic X-ray imaging of a selected cross sectional tomographic plane at a particular site of interest, comprising:

head fixator means for positioning and aligning the patient's head accurately at a reference position and rotational orientation.

measuring means connected to the head fixator for measuring the location of the site relative to said reference position and rotational orientation, translation and rotation means connected to the head fixator means, for permitting measured translation of the head fixator means along X, Y and Z axes and measured rotation of the head fixator means so as to locate the site precisely at an intersection point which is the isocenter of X-ray intersection in the plane of the X-ray center axes.

2. The apparatus of claim 1, wherein the head fixator has means for rotation about a vertical axis, and wherein the measuring means includes an arm rotatable about said vertical axis and having an end extending radially outwardly and to a position adjacent to the patient's head, with pointer means connected to the end of the arm for taking an inward radial measurement to the site on the patient relative to a reference position and for taking a vertical measurement to the site along the arm relative to the said reference position, and the arm having means for measuring the rotational position of the site relative to a reference plane, whereby with the arm and pointer means, polar coordinates of the position of the site relative to the vertical axis and the reference plane can be determined, along with height of the site relative to said reference position.

3. The apparatus of claim 1, further including angle correction means for determination of corrected X, Y and Z axis positions and rotational orientation for the head fixator means such that particular bone structure at the site of interest is substantially perpendicular to said selected cross sectional plane.

4. The apparatus of claim 3, wherein the site of interest is a potential dental implant site on the patient's mandible or maxilla, and wherein said means for determination includes means for determining the corrected positions such that the patient's mandibular arch at the site of interest is substantially tangent to the plane of X-ray center axes.

5. A method for positioning the head of a patient accurately for tomographic X-ray imaging of a selected cross sectional plane at a particular site of interest, comprising,
selecting a site of interest in the head and a desired cross sectional plane at the site for tomographic X-ray imaging,
using a head fixator device, aligning the patient's head on a tomographic X-ray imaging apparatus, relative to a reference position including a reference cranial orientation and reference X, Y and Z axis positions,
measuring the location of the site of interest relative to the reference position and reference orientation,
performing calculations to align the desired X, Y, Z and rotational adjustments of the head fixator device in order to place the site at an intersection point which is the isocenter of X-ray intersection in the plane of the tomographic X-ray procedure containing all X-ray center axes, and to place the orientation of the head such that the selected cross sectional plane at the site is substantially perpendicular to the plane of the tomographic X-ray procedure, and
making adjustments to the position of the head fixator device with respect to X, Y and Z axes as well as rotational orientation in accordance with the calculations, and placing the patient in the head fixator device for tomographic X-ray imaging of said selected cross-sectional plane at the site.

6. The method of claim 5, wherein the step of aligning the patient's head includes using a pair of ear posts to engage the meatus at each side of the head.

7. The method of claim 5, wherein the measuring step includes making a direct measurement along the Z or vertical axis, and measuring X at Y positions using polar coordinates, by measuring an angle from the patient's midsagittal plane to the site and a radial distance to the site from an axis which is the center of rotation of the measured angle.

8. The method of claim 5, wherein the tomographic cross-sectional image is of a potential dental implant site on the mandible or maxilla, and wherein the performing of calculations includes the selection of an appropriate polynomial representing the shape of the mandibular curve of the particular patient, the inputting of values representing said polynomial of the patient into the calculations, and the performing of the calculations such that a tangent to the mandibular curve of the patient at the site is substantially parallel to the plane of the X-ray procedure.

9. The method of claim 5, wherein the head fixator device includes a pair of ear posts for engaging the external auditory meatus bilaterally of the patient to prevent turning of the head, and a nasion engaging device on the head fixator for immobilizing the patient with respect to rotation of the head about the transmeatal line.

10. A method for positioning the head of a patient accurately for X-ray imaging of a selected site of interest, comprising,
selecting a site of interest in the head of the patient, using a head fixator device, aligning the patient's head on an X-ray imaging apparatus, relative to a reference position including a reference cranial orientation and reference X, Y and Z axis positions,
measuring the location of the site of interest relative to the reference position and reference orientation,
removing the patient from the head fixator device,
determining a new desired position for the head fixator device in X, Y and Z positions and with rotational orientation as desired, in order to place the site of interest at a proper position in the path of X-rays to form an image of the site of interest,
making adjustments to the position of the head fixator device with respect to X, Y and Z axes as well as any needed rotational adjustments in accordance with the determination, and placing the patient in the head fixator device to correctly position the site of interest for X-ray imaging of the site.

11. The method of claim 10, wherein the step of aligning the patient's head includes using a pair of ear posts to engage the meatus at each side of the head.

12. The method of claim 10, wherein the measuring step includes making a direct measurement along the Z or vertical axis, and measuring X at Y positions using polar coordinates, by measuring an angle from the patient's midsagittal plane to the site and a radial distance to the site from an axis which is the center of rotation of the measured angle.

13. The method of claim 10, wherein the X-ray imaging comprises tomographic X-ray imaging and wherein a tomographic cross-sectional X-ray image to be taken is of a potential dental implant site on the mandible or maxilla, and wherein said determination includes the selection of an appropriate polynomial representing the shape of the mandibular curve of the particular patient, the inputting of values representing said polynomial of the patient, and the performing of calculations to align the desired X, Y and Z and rotational adjustments of the head fixator device in order to place the site at an intersection point which is the isocenter of X-ray intersection in the plane of the X-ray procedure containing all X-ray center axes, and such that a tangent to the mandibular curve of the patient at the site is substantially parallel to the plane containing all X-ray center axes in the X-ray procedure.

14. The method of claim 10, wherein the head fixator device includes a pair of ear posts for engaging the external auditory meatus bilaterally to prevent turning of the head, and a nasion engaging device on the head fixator for immobilizing the patient with respect to rotation of the head about the transmeatal line.

15. A system for positioning the head of a patient accurately for X-ray imaging of a selected site of interest, comprising,
head fixator means for positioning and aligning the patient's head accurately at a reference position and rotational orientation, measuring means connected to the head fixator means for measuring the location of the site relative to said reference position and rotational orientation, and translation and rotation means connected to the head fixator means, for permitting measured translation of the head fixator means along X, Y and Z axes and measured rotation of the head fixator means so as to locate the site precisely at a desired position in the path of X-rays in the X-ray procedure.

* * * * *

UNITED STATES PATENT AND TRADEMARK OFFICE
CERTIFICATE OF CORRECTION

PATENT NO. : 4,974,243
DATED : November 27, 1990
INVENTOR(S) : McArdle et al.

Figure 14A:
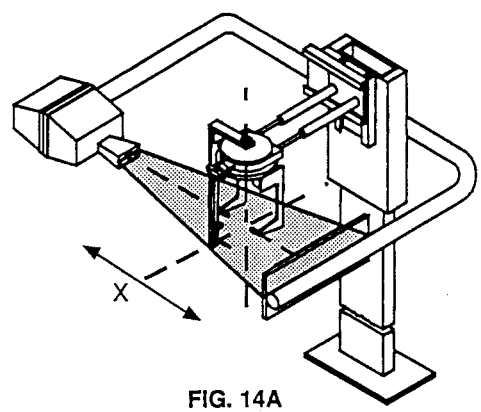
FIGS. 14A, 14B and 14C are frontal perspective views of the device, with 14A and 14C illustrating the bounds of the X-ray field.
Figure 14B:
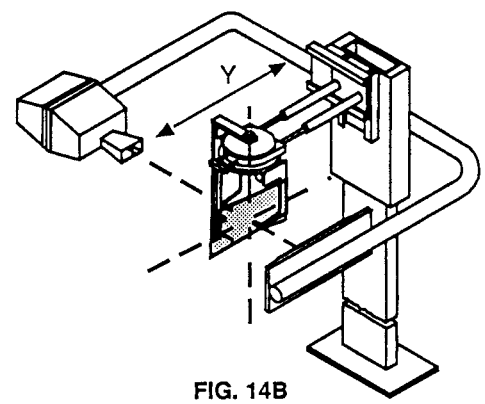
Figure 14C:
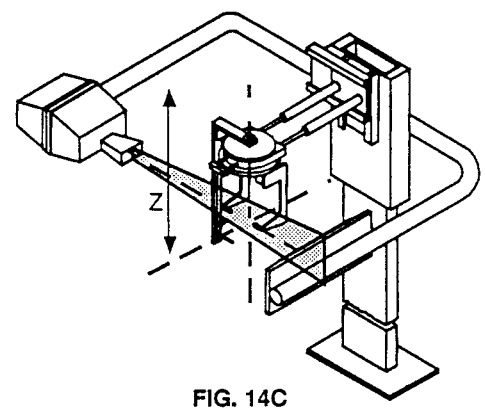

It is certified that error appears in the above—identified patent and that said Letters Patent is hereby corrected as shown below:

Column 4, line 35, "illustrated in FIG." should read --illustrated in FIG. 14.--.

Column 6, line 59, "the 10 slide" should read --the slide--.

Column 9, line 4, "$x^{2+(4E)x3}$" should read --$x^2+(4E)x^3$--.

Column 9, line 16, "$Slope_{Q=f(x1)}=B+[(2C)*x_1]$" should read --$Slope_Q=f'(x_1)=B+[2C)*x_1]$--.

Signed and Sealed this

Twenty-sixth Day of May, 1992

Attest:

DOUGLAS B. COMER

Attesting Officer      Acting Commissioner of Patents and Trademarks